United States Patent [19]
Dumoulin et al.

[11] Patent Number: 5,807,575
[45] Date of Patent: Sep. 15, 1998

[54] MANUFACTURE OF CROSS-LINKED AMYLOSE USEFUL AS A EXCIPIENT FOR CONTROL RELEASE OF ACTIVE COMPOUNDS

[75] Inventors: Yves Dumoulin, Sainte-Julie; François Carriere, Ile des Soeurs; André Ingenito, Mont Saint-Hilaire, all of Canada

[73] Assignee: Rougier Inc., Montreal, Canada

[21] Appl. No.: 800,518

[22] Filed: Feb. 14, 1997

[51] Int. Cl.$^6$ ................................. A61K 9/22; A61K 9/14
[52] U.S. Cl. ........................... 424/464; 424/468; 424/489; 424/493
[58] Field of Search ........................... 424/464, 468–470, 424/488, 489, 493

[56] References Cited

U.S. PATENT DOCUMENTS

| | | |
|---|---|---|
| 2,987,445 | 6/1961 | Levesque . |
| 3,087,860 | 4/1963 | Endicott . |
| 3,622,677 | 11/1971 | Short et al. ............................. 424/361 |
| 4,369,308 | 1/1983 | Trubiano ................................. 536/106 |
| 4,667,590 | 5/1987 | Balaam et al. ............................ 99/470 |
| 5,456,921 | 10/1995 | Mateescu et al. ...................... 424/465 |

FOREIGN PATENT DOCUMENTS

| | | |
|---|---|---|
| 0 499 648 A1 | 8/1992 | European Pat. Off. . |
| WO94/02121 | 2/1994 | WIPO . |
| WO94/21236 | 9/1994 | WIPO . |

OTHER PUBLICATIONS

"Preparation and Evaluation of Sustaine Release Tablets Prepared with αStarch", Nakano et al., *Chemical & Pharaceutical Bulletin*, vol. 35, 1987, pp. 4346–4350.

"Modified starches as hydrophilic matrices for controlled oral delivery. II. In vitro drug release evalution of thermally modified starches", Herman et al., *International Journal of Pharmaceutics*, 56, (1989), pp. 65–70.

"In vitro evaluation of modified starches as matrices for sustained release dosage forms", van Aerde et al., *International Journal of Pharmaceutics*, 45 (1988), pp. 145–152.

"Crosslinked Starch as Sustained Release Agent", Visavarungroj et al., *Drug Development and Industrial Pharmacy*, 16(7), 1990, pp. 1091–1108.

"Amylose as a coating for drug delivery to the colon: Preparation and in vitro evaluation using glucose pellets", Milojevic et al., *Journal of Controlled Release*, 38 (1996), pp. 85–94.

"Polymorphic Transitions of Amylose–Ethanol Crystalline Complexes Induced by Moisture Exchanges", Le Bail et al., *Starch*, 47 (1995), Nr. 6, pp. 229–232.

"Investigation of the Crystalline, V Amylose Complexes by High–Resolution $^{13}C$ CP/MAS NMR Spectroscopy", Veregin et al., *Macromolecules*, 1987, 20, pp. 3007–3011.

"Characterization of the Crystalline A and B Starch Polymorphs and Investigation of Starch Crystallization by High–Resolution $^{13}C$ CP/MAS NMR ", Veregin et al., *Macrololecules*, 1986, 19, pp. 1030–1034.

*Primary Examiner*—Michael P. Woodward
*Assistant Examiner*—Brenda G. Brumback
*Attorney, Agent, or Firm*—Bacon & Thomas

[57] ABSTRACT

A process for the manufacture of a slow-release excipient consisting mainly of cross-linked amylose in the form of solid particles, for use in the preparation of tablets or pellets. A starch containing a high amount of amylose (high amylose starch) is first subjected to a gelatinization. The gelatinized high amylose starch is then cross-linked with 1 to 5 g of a cross-linking agent per 100 g of dry-based gelatinized high amylose starch in an alkali medium, thereby forming a reaction medium containing a reaction product consisting of a cross-linked high amylose starch slurry. The obtained reaction medium is neutralized, thereby forming by-products mainly consisting of salts, which are removed from the reaction medium. The recovered cross-linked high amylose starch slurry is then subjected to a thermal treatment at a temperature of at least 60° C. and the thermally treated product is dried to obtain the requested slow release excipient. This process is economical and industrially advantageous since it is carried out in an aqueous medium.

16 Claims, No Drawings

MANUFACTURE OF CROSS-LINKED AMYLOSE USEFUL AS A EXCIPIENT FOR CONTROL RELEASE OF ACTIVE COMPOUNDS

FIELD OF THE INVENTION

The present invention relates to a process for the manufacture of a tablet excipient for use in the pharmaceutical industry.

More particularly, it relates to an economical process for the industrial manufacture of a slow release excipient mainly composed of cross-linked amylose, which is useful in the preparation of controlled release dosage forms by direct compression.

BACKGROUND OF THE INVENTION

Tablets are considered as the most advantageous form of administration. In addition to the active ingredients, the tablets usually contain several inert compounds referred to as "excipients", in sufficient amount to accomplish the desired effect.

Excipients are generally classified by their functions and the major types of excipients that are presently used consist of fillers or diluents, binders, disintegrants, binder-disintegrants, lubricants and glidants [see for example "Compressed tablets" by B. B. Sheth et al in Pharmaceutical dosage forms, vol. 1, chap. 3, p 109–185, H. A. Lieberman and L. Lachman, Marcel Dekker, New York 1980]. Other specific excipients that are commonly used include colorants, sweeteners, flavours and the like. Further specific excipients that are commonly used in this field consist of "slow release" excipients that are usually made of polymers and are used to prolong and sustain the release of the active ingredients [see for example U.S. Pat No. 3,087,860; U.S. Pat. No. 2,987,445 and Pharm. Acta. Helv., 55, 174–182].

As excipients, most of polysaccharidic materials are of interest and starch is one of the most interesting polymer used in this field. Starch is a natural carbohydrate and is considered to be the most important source of energy in plants. It is composed of two distinct fractions: amylose which is a non-ramified fraction containing about 4,000 glucose units joint by $\alpha$-1,4 links, and amylopectin which is a branched fraction composed of about 100,000 glucose units. Starch is a natural occurring diluent but it can also be used as a tablets disintegrant agent. Starch can be modified through physical, chemical or enzymatic processes.

Pregelatinized common starch containing usually 20 to 30% w/w of amylose, can be used in the place of starch as a filler and binder-disintegrating agent. It is also reported that pregelatinized starch may be used as a sustained release hydrogel [Nakano M. et al, Preparation and evaluation of sustained release tablets prepared with $\alpha$-starch, Chem. Pharm. Bull. 35 (1987) 4346–4350]. However, tablets made with common pregelatinized starch (containing 25% of amylose w/w) and tested in vitro have been reported to split into two parts, thereby resulting in a burst of drug release because of an increase in the free surface area [Herman J. and Remon J. P., Modified starches as hydrophillic matrices for controlled oral delivery. II. In vitro drug release evaluation of thermally modified starches, International Journal of Pharmaceutics, 56 (1989) 65–70].

Modified and/or cross-linked starches are known to be powerful disintegrating agents with poor binding properties [see U.S. Pat. No. 3,622,677 and U.S. Pat No. 4,369,308]. Usually, starch is cross-linked to increase its resistance to shear or to prevent gelatinization when heated, thereby permitting utilization of cross-linked starch granules in applications which would destroy granules of unmodified starch. The preparation of modified and/or cross-linked starch is well known in the art and such preparation are described in numerous text books and publications [see, for example, "Starch derivatives: production and uses" by M. W. Rutenberg and D. Solarek in Starch chemistry and technology, 2nd ed., chap. x, p. 311–379, R. L. Whistler, J. N. BeMiller and E. F. Paschall, Academic Press, 1984]. It has also been reported that cross-linked gelatinized starch may be used as a sustained release agent. However, an increase in the degree of cross-linking of gelatinized starch causes an increase in the swelling of the tablet, a decrease in the tablet gel strength and, consequently, an increase in the tablet drug release rate [Van Aerde P. and Remon J. P., In vitro evaluation of modified starches as matrices for sustained release dosage form, International Journal of Pharmaceutics, 45, 145–152 (1988)].

Pregelatinized waxy corn starch containing almost 100% of amylopectin w/w and almost no amylose, either cross-linked or not, is reported to form a gel layer during hydration and to decrease the in vitro drug release rate. However, the swollen gel layer of such amylose free starch consisting exclusively of amylopectin is reported to be very weak and the In Vivo tablet erosion may considerably accelerate the drug release [Herman J. and Remon J. P., Modified starches as hydrophillic matrices for controlled oral delivery. II. In vitro drug release evaluation of thermally modified starches, International Journal of Pharmaceutics, 56 (1989) 65–70]. Consequently, those products can be used as filler and disintegrant but are not recommended to be used as a hydrophillic matrix in a sustained release formulation [Visavarungroj N., Herman J. and Remon J. P., Cross-linked starch as sustained release agent, Drug Development and Industrial Pharmacy, 16, (7), 1091–1108, 1990].

It is known that native or pregelatinized high amylose starch (containing 70% or more of amylose w/w) are not suitable as a hydrophillic matrix in a sustained release formulation. Tablets made of pregelatinized high amylose starch and placed into dissolution medium do not form an obstructive gel layer at the surface of the tablet, but swell progressively with the formation of a porous spongy layer. This layer is reported to erode quickly, thereby resulting in a fast drug release [Herman J. and Remon J. P., Modified starches as hydrophillic matrices for controlled oral delivery. II. In vitro drug release evaluation of thermally modified starches, International Journal of Pharmaceutics, 56 (1989) 65–70]. However, it is also reported that a mixture of amylose and ethylcellulose may be used in the formulation of an $\alpha$-amylase resistant coating for the drug delivery to the human large intestine [Milojevic S.et al, Amylose as a coating for drug delivery to the colon: Preparation and in vitro evaluation using glucose pellets, Journal of Controlled Release 38, 85–94 (1996)].

Modified and/or cross-linked short amylose chains resulting from the enzymatic debranching of starch prior to or after chemical modification, thereof have already been used as binder-disintegrants in tablets. It is reported that the binding-disintegrating properties of such excipients increase with the quantity of short amylose chains produced by the hydrolyse of amylopectine [see, for example, European laid-open patent EP-A-449,648 to NATIONAL STARCH].

Cross-linked amylose having a cross-linking degree ranging from 1 to 10, is known to be particularly useful as a controlled release excipient for the preparation of tablets by direct compression (see U.S. Pat. No. 5,456,921 to LABOP- HARM INC.). It is also known that α-amylase can be incorporated into tablets made of cross-linked amylose in order to increase the dissolution rate of low soluble drugs. (See International laid-open patent application WO94/02121 to LABOPHARM INC.).

Cross-linked amylose having a cross-linking degree of 6 to 30 is further known to be useful as a binder and/or disintegrant excipient for the preparation of tablets by direct compression (see international laid-open patent application WO94/21236 to LABOPHARM INC.). The binding properties of this product are reported to be definitively superior to starch. The quality of the binding and the controlled release properties of cross-linked amylose are closely related to the cross-linking degree and to the relative amount of amylose present in the starch used for the manufacture.

In all these patent and laid-open applications of LABOPHARM INC., a laboratory scale process of manufacture of cross-linked amylose is disclosed, which consists of reacting in a planetary mixer a product distributed by Sigma Chemicals, which is called amylose and consists of a corn starch containing more than 70% of amylose w/w, with epichlorohydrin in an alkaline medium. The obtained product is washed on a Büchner funnel with a solution of acetone and dried with pure acetone. About 40 Kg of acetone are needed to manufacture 1 Kg of cross-linked high amylose starch. The manufacturing process described in these patent and applications is effective but of academic interest only.

It is well known in the art that the use of alcohols and/or acetone for the treatment of starch is reported to complex the amylose fraction [see for example in P. Le Bail et al, *"Polymorphic transitions of amylose-ethanol crystalline complexes induced by moisture exchanges"*, Starch/Stärke 47, (1995) no. 6 p. 229–232, 1995]. The morphological form of complex amylose, called V form, can be revealed by $C^{13}$ CP/MAS NMR spectroscopy [see for example, R. P. Verigin et al, *"Investigation of the crystalline V amylose complexes by high resolution $C^{13}CP/MAS$ NMR spectroscopy"*, Macromolecules, vol. 20, no. 12, p. 3007–3012, 1987]. Product manufactured according to the process described hereinabove wherein acetone is used for washing and drying the product, have the adequate properties. However, this manufacturing process cannot be economically and safely transposed to an industrial scale. Much more, in the context of growing attention paid to the environmental and health care, many efforts are presently devoted to the development of aqueous processes and to the employment of ingredients like trisodium trimetaphosphate, which is qualified as more acceptable by the Food and Drug Administration (FDA) and other health organisations, as cross-linking agents. This context of environmental and health care forces the pharmaceutic industry like the food industry to employ GRAS ingredients (generally recognized as safe) and also places emphasis to the development of "more ecological products".

SUMMARY OF THE INVENTION

The object of the present invention is to provide an economical process for the industrial manufacture in an aqueous medium, of cross-linked amylose having the same desired product morphological form and properties as presently obtained by acetone treatment.

The present invention is based on the discovery that the properties desired for the cross-linked amylose to make it useful as a slow release excipient, are related to the product capacity to shift from the V form to the B form during hydration. It is also based on the discovery that it is possible to obtain the requested form of cross-linked amylose without using acetone. It is further based on the discovery that the desired product properties are unexpectedly depending on the process temperature.

Thus, the invention as broadly defined provides a process for the industrial manufacture of a slow-release excipient consisting mainly of cross-linked amylose having controlled release properties for use in the preparation of tablets or pellets, which process comprises:

(a) subjecting a starch containing a high amount of amylose, hereinafter called "high amylose starch", to a gelatinization;

(b) cross-linking the gelatinized high amylose starch with 1 to 5 g of a cross-linking agent per 100 g of dry-based gelatinized high amylose starch in an alkali medium thereby forming a reaction medium containing a reaction product consisting of a cross-linked high amylose starch slurry;

(c) neutralizing the reaction medium obtained in step (b), thereby forming by-products mainly consisting of salts, removing the by-products from said reaction medium to recover the cross-linked high amylose starch slurry;

(d) subjecting the cross-linked high amylose starch slurry to a thermal treatment at a temperature of at least 60° C.; and (e) drying the thermally treated product obtained in step (d) to obtain the requested slow release excipient consisting mainly of cross-linked amylose in the form of solid particles.

In accordance with a preferred embodiment of the invention, the cross-linked high amylose starch slurry recovered after completion of step (c) is concentrated at a concentration ratio lower than or equal to 10% w/w of solids.

This optional concentration step can be carried out in addition to the thermal treatment step (d) or can replace it, if the concentration temperature is sufficient to achieve proper thermal treatment of the slurry.

DETAILED DESCRIPTION OF THE INVENTION

Thus, the process according to the invention for the manufacture of a slow-release excipient consisting mainly of cross-linked amylose comprises a plurality of steps which will be described in greater details hereinafter.

Step (a): Gelatinization

Micellar crystallites held together by hydrogen bonding between amylopectin and amylose are responsible for the integrity of starch granules. When an aqueous suspension of starch is heated to a certain temperature, the hydrogen bonding weakens and the granule swells until collapsing. This is called "gelatinization".

Numerous methods of gelatinization of starch are well known in the art, including direct or indirect heating of an aqueous dispersion of starch, by chemical treatment of such dispersion using strong alkalies, or a combination of mechanical and heat treatment. Pregelatinized starch is also known to be soluble in cold water. At first sight, one could say that the gelatinization of starch is not desirable to obtained a controlled release excipient. However, in accordance with the invention, it has been found that the gelatinization of the high amylose starch used as starting material is essential to permit leaching of the amylose from the starch granules prior to the reaction with a cross-linking agent, and thus to get the controlled release property.

In accordance with the invention, gelatinization of the high amylose starch is preferably realized by chemical treatment using sodium hydroxide or by thermomechanical treatment using a scraped surface heat exchanger.

The chemical treatment may consist of adding a sodium hydroxide solution to a dispersion of high amylose starch containing 5 to 25% w/w at a temperature range of 20° to 65° C. in order to obtain a minimal concentration of 1% w/w of alkali until leaching of amylose occurs and reaches an equilibrium.

The thermomechanical treatment may consist of treating an aqueous dispersion containing 5 to 16% w/w of high amylose starch in a scraped-surface heat exchanger at a temperature range of 110° to 160° C. for 5 to 60 minutes depending on the amylose content, temperature and quantity introduced.

Steps (b) and (c): Cross-linking reaction and neutralization

Cross-linking represents a powerful tool for modifying starch. Usually, starch granules are cross-linked to increase resistance to shear or to prevent gelatinization when heated, thereby permitting utilization of starch granules in applications which would destroy granules of unmodified starch.

As aforesaid, in accordance with the invention, it has been discovered that the cross-linking of starch granules as such is not desirable. More specifically, it has been found that the gelatinization of high amylose starch is actually required in order to prepare a product possessing the desired controlled release property.

The cross-linking of high amylose starch may be realized according to procedures described in the prior art. The reaction conditions employed will vary with the type and amount of the cross-linking agent that is used, as well as the batch size, the starch content, the sodium hydroxide concentration, and the like. As cross-linking agents, use can be made of any cross-linking agent accepted in the pharmaceutical and food industries, such as, for examples, trisodium trimetaphosphate, epichlorohydrin, adipic-acetic anhydride and phosphorus oxychloride.

In practice, the pH of the gelatinized starch (5 to 25% w/w) can be adjusted in the range of 10 to 14 and the product temperature adjusted in the range of 20° to 65° C. Cross-linking can be carried out by adding from 1 to 5 g by weight of cross-linking agent per 100 g (dry based) of gelatinized high amylose starch under stirring condition at a temperature ranging from 20° to 65° C. The reaction time depends on the conditions employed and may vary from 0.5 to 40 hours. After the completion of the reaction, the reaction medium containing the requested cross-linked high amylose starch slurry is neutralized to a pH range of 2 to 9.

Step (c): Removal of by-products

The cross-linked reaction carried out in an alkaline medium and followed by a neutralization leads to the formation of by-products mainly consisting of salts. Numerous methods can be used to remove salts from the aqueous slurry of cross-linked amylose, including electrodialysis, filtration, centrifugation, decantation, continuous ultrafiltration (diafiltration) and the like. Those methods may use solely water or may use a mixture of water and alcohol.

In accordance with the present invention, any of those known methods can be used. However, the salts contained in the cross-linked amylose slurry are preferably removed by aqueous continuous ultrafiltration. Water-transport is achieved by viscous flow through pores, driven by a moderate applied pressure. Small solutes like salts pass through the membrane, but the macrosolutes and colloids are retained. Industrial ultrafiltration was initially developed for the treatment of waste water. Its applicability has now widened considerably to include food processing, sugar refining, vegetable protein processing, textile industry, pulp and paper industry and in many more applications. Numerous types of polymeric membrane can be used for diafiltration, including cellulose acetate membrane, composite membrane, mineral or ceramic membrane, polysulfone membrane and others. Membrane pore sizes may vary, in function of the size of component that have to be separated, from 1000 Da to 0.45 $\mu$m and probably more. The continuous ultrafiltration mode (diafiltration) consists of continuously adding fresh water to the slurry, at the same rate that the permeate is removed, in view to maintain a constant volume.

In accordance with the invention, even if any one of the polymeric membrane mentioned hereinabove may be used, diafiltration is preferably carried out with hollow fibres polysulfone membrane with pore sizes in the range of 10000 Da and 0.2 $\mu$m. The cross-linked amylose slurry is diluted in the range of 0.1% to 3% w/w and the product temperature may vary from 20° to 65° C. The water quantity used to remove the by-products is related to the degree of purity desired and may vary from 50 to 200 L of fresh water for 1 Kg of product (dry base).

Optional step: Concentration

The reaction product recovered after diafiltration can be dried as such. However, it is preferable, from an economic standpoint, to concentrate the product. Concentration of the cross-linked amylose slurry can be realized by numerous methods including ultrafiltration, freezing concentration followed by centrifugation, evaporation, precipitation with organic solvent like alcohol or acetone followed by centrifugation or decantation and evaporation under vacuum.

In accordance with the present invention, any one of those concentration methods can be used herewith. However, the cross-linked high amylose starch slurry is preferably concentrated by evaporation under vacuum. The inlet temperature within the evaporation may vary from room temperature to 100° C. The outlet temperature may vary from 50° to 100° C., depending on the vacuum applied and the plate temperature. The vacuum may vary from 0 to 29 inch of Hg, and the temperature of the plate used for the evaporation may vary from 80° to 120° C. The initial concentration of the cross-linked high amylose starch slurry can vary in the range 0.1% to 7.9% w/w and the final product concentration may reach 10% w/w.

Step (d): Thermal treatment

As discussed in greater detail in example 1, it has surprisingly been discovered that the properties that the cross-linked amylose must have to be useful as an excipient for drug controlled release, are dependent on the intensity of a heat treatment applied to the aqueous slurry just before the precipitation step or before the spray drying.

More particularly, it has been found that if the aqueous reaction product that is prepared is kept at a temperature in the range of 1° to 20° C. or the same product after concentration by a freeze concentration process or by evaporation is cooled down to below 20° C., it must subsequently be thermally treated at a temperature higher than 60° C. in order to have the desired properties.

The thermal treatment temperature is dependent on the quantity of cross-linking agent used for the reaction, on the product concentration and the process temperature of previous steps. In practice, the higher is the cross-linking degree, the higher shall be the thermal treatment temperature. In all cases, the thermal treatment shall however be carried out at a temperature higher than 60° C. for a time sufficient to ensure proper "transformation" of the morphology of the cross-linked amylose into the imperfect V-form that seems to be the one required to permit subsequent shifting to the B form during hydration, and thus to achieve the requested results (see example 1 thereinafter).

By way of example with a cross-linked high amylose starch having a cross-linking degree equal to 2% w/w, the thermal treatment can be carried out at 90° C. for 2 minutes.

Step (e) Drying

The thermally treated product can be dried by lyophilization, by spray drying techniques using a spray nozzle or atomization disc or in a heated chamber after the substitution of water for alcohol or acetone.

Lyophilization:

Cross-linked amylose slurry, in the form of a slurry having a concentration ranging from 0.1 to 10% w/w, can be frozen in a $CO_2$ chamber or in a freezer, or directly in the lyophilization chamber, and then lyophilized at a set point temperature in a range from 10° to 40° C. for 24 to 72 hours. The dried product can be pulverized in a way to obtain particular size from 20 to 500 µm.

Substitution of alcohol or acetone for water prior to air drying

The cross-linked amylose slurry at a concentration in the range of 4 to 20% w/w, must be treated under high stirring conditions at a temperature range from 20° to 60° C. in order to obtain the controlled released property. Then, the product can be treated with subsequent addition of alcohol or acetone followed by filtration or centrifugation in order to replace the water. The product may be air dried at room temperature, in a conventional oven or in an air circulating oven at a temperature range from 20° to 105° C. for a period of time related to the temperature that is used. The dried product can be pulverized in a way to obtained particular size from 20 to 500 µm.

Spray drying:

As mentioned hereinabove, the cross-linked amylose slurry at a concentration in the range of 0.5 to 10% w/w can be spray-dried using a spray nozzle or a rotating disk. In such case, the inlet temperature can be in the range of 175° to 350° C. and the outlet temperature in the range of 60° to 135° C. In order to reduce the viscosity of the product prior to spray drying, the product can be treated using alcohol or acetone in a concentration ranging from 1 to 35% w/w. The addition of alcohol or acetone to the cross-linked amylose slurry (0.5 to 15% w/w) can be carried out under high stirring conditions at a temperature ranging from 20° to 60° C. Then, the product can be cooled down to a temperature in the range from 1° to 10° C.

Optional step: Wet granulation

The size of the particles of the cross-linked amylose powder obtained by spray-drying are smaller then 50 µm. To enlarge the particle size and obtain uniform particles which will flow through the industrial tablet machine hopper and feed frame into the dies, the so obtained particles can be subjected to wet granulation. Such a wet granulation also permits to remove residual alcohol from the product if the product was treated with alcohol prior to being subjected to spray drying. The powder recovered from the spray dryer can be wet granulated in line using a fluid bed granulator. Alternatively, they can be granulated separately in a fluid bed or in a V-blender.

In accordance with the invention, any one of these granulation techniques can be used. However, the cross-linked amylose powder is preferably granulated using a separate fluid bed granulator.

In practice, the wet granulation of the powder can be realized in three steps. The first step consists of fluidizing and humidifying the powder obtained from the spray dryer at a temperature ranging from 20° to 40° C. with a dew point in the range of 10° to 25° C. for a period of time sufficient to reach more than 4% of moisture content. Then, water may be introduced into the fluid bed by a spray nozzle at a rate from 80 to 150 ml/min and the granulation may be realized in a temperature range from 20° to 40° C. The water quantity and the granulation time are related to the previous parameters and to the particle size desired. The last step consists of drying the product. This step may be carried out in the fluid bed granulator at a temperature in the range from 40° to 60° C. until desirable moisture content is obtained.

The invention and the way it can be reduced to practice will be better understood upon reading the following non-restrictive examples.

TEST METHODS

The following procedures were used as test methods to evaluate the properties of the products prepared in the examples.

Controlled release property

Controlled release property of tablets made of cross-linked high amylose starch was evaluated using the "in vitro," dissolution test.

Preparation of the tablets:

Tablets having a diameter of 13 mm and a thickness of 2.9 mm were prepared by direct compression of a powder mixture of 400 mg of cross-linked high amylose starch and 100 mg of acetaminophen as a model drug. The compression was carried out in an hydraulic press at 2.4 T/cm$^2$.

"In vitro" tablets dissolution:

The so prepared tablets were placed individually in 1 L of phosphate buffer in accordance with USP 23 p. 1791 (test <711>, 37° C. at pH=7) in a Distek dissolution apparatus equipped with paddles rotating at 50 rpm. The drug release was monitored spectrophotometrically at 244 nm, recorded and analyzed with a Hewlett Packard dissolution system.

Morphological characterization of cross-linked high amylose starch by $^{13}C$ CPMAS The morphological characterization of the prepared product was carried out according to the following procedure:

Starch can be found in the nature under three different polymorphic forms (A, B and C) and the solids state NMR can be used to reveal the structure of the polymorphs. From literature data (Veregin, R. P.; Fyfe, C. A.; Marchessault, R. H. and Taylor, M. G. in *Macromolecules,* 1986, 19, 1030) one knows that the A form is distinguished by a sequence of bands in which the original signal for the C1 is a triplet and a doublet for the B form.

Another polymorphic form of amylose called the V form can be obtained when the starch is treated with alcohols. The V amylose complex gives rise to a different pattern (Veregin, R. P.; Fyfe, C. A. and Marchessault, R. H. in *Macromolecules,* 1987, 20, 3007) than that obtained for the A and B forms. Usually, the bands are shifted downfield, the resonance are broader and the C1 is represented by a singlet.

Spectra of cross-linked high amylose starch powder and in the form of press pellets of 200 mg were obtained at 75.34 MHZ using a Chemagnetics CMX-300 spectrometer. The pulse sequence used was a standard cross-polarization sequence with a $^1H$ p/2 pulse width of 4.25 µs (corresponding to a $g_HB_{1H}$ of 62.5 KHZ), a contact time of 1.5 ms and a recycle delay of 2 s. Typically, 500–1000 transients were accumulated. Magic-angle spinning was performed at 3.5–4 KHZ.

Particle size distribution:

The particle size distribution was determined according to USP 23 p. 1822 (test method <811>). A quantity of 50 g of granulated product was placed for 20 minutes in a Ro-tap® apparatus equipped with screen size of 75, 150, 250, 355 and 850 µm. The particle size distribution is expressed as relative product weigh on each screen.

EXAMPLE 1

Preparation of cross-linked high amylose starch using a chemical gelatinization pretreatment and epichlorohydrin as cross-linking agent.

Gelatinization:

A high amylose starch containing 70% w/w of amylose was first gelatinized. To do so, 39.4 Kg of sodium hydroxide solution at 11.9% w/w were introduced under agitation in a slurry consisting of 24 Kg of high amylose starch and 53 Kg of water. The gelatinization was carried out 50° C. for 20 minutes in a 200 L GOAVEC® crystallization tank.

Cross-linking reaction of the high amylose starch with epichlorohydrin.

Under intensive stirring, 0.48 Kg of epichlorohydrin was introduced into the 116 Kg of the gelatinized high amylose starch recovered in the previous step. The reaction was carried out at 50° C. for 1 hour. After reaction, the reaction medium was diluted with 72 Kg of water at 60° C. Then, the mixture was neutralized with an acetic acid solution (37.5% w/w) to obtain a pH below 8. The neutralized product was diluted with 680 Kg of water at 50° C. and cooled down to 4° C. Then, it was kept at that temperature until the next step.

Removal of by-products and concentration:

The product recovered from the previous step was diluted under agitation with 200 Kg of water at 50° C. and the mixture was heated up to 50° C. A diafiltration was realized with an ALFA-LAVAL® apparatus model UFS-6 equipped with 6 hollow fibres polysulfone membrane of 60 mils opening and surface of 25 square feet with pore sizes of 50000 Da. An average of 4000 Kg of water at 50° C. was used to remove the by-products (mainly consisting of sodium acetate). Then, the resulting product was concentrated up to 3.8% w/w by ultrafiltration. The recovered product was cooled down to 4° C. and was maintained at that temperature until the next step.

Thermal treatment:

As briefly discussed hereinabove, the properties of the prepared cross-linked high amylose starch that are required to make it useful as an excipient for drug controlled release are surprisingly dependent to the thermal treatment applied to the slurry just before spray drying. In order to demonstrate this dependency, cross-linked high amylose starch prepared as disclosed hereinabove was treated at different temperatures as is disclosed in the following paragraphs called examples 1a, 1b and 1c respectively.

EXAMPLE 1a

Thermal treatment at 90° C.

A slurry of cross-linked high amylose starch recovered from the diafiltration step disclosed hereinabove was heated up to 90° C. under stirring and kept at that temperature for 2 minutes. Then, the product was cooled down to 50° C. under stirring and spray dried at 3,8% of solids in a Niro spray dryer model P6.3 of water evaporating capacity of 50 Kg/h, equipped with a atomizer disc and having an inlet temperature of 300° C. and an outlet temperature of 120° C.

EXAMPLE 1b

Thermal treatment at 60° C.

By proceeding in the same manner as in the example 1, the product recovered from the diafiltration step was thermally treated under stirring for 2 minutes at 60° C. Then, it was spray dried in the very same manner.

EXAMPLE 1c

Thermal treatment at 50° C.

By proceeding in the same manner as in the example 1, the product recovered from the diafiltration step was thermally treated under stirring for 2 minutes at 50° C. Then, it was spray dried in the very same manner.

The controlled release properties of the cross-linked high amylose starches, prepared as described in examples 1a, 1b and 1c, were evaluated using the above described tests methods. The obtained results are reported in the following table I.

TABLE I

| | Time (h) required to release the following % of the initial drug content of the tablet | | |
|---|---|---|---|
| | 30% | 60% | 90% |
| Example 1a | 3.0 | 9.0 | 22.0 |
| Example 1b | 1.0 | 3.0 | 6.0 |
| Example 1c | <1 | <1 | <1 |

The dissolution test results reported in table I show that the product of example 1a that was subjected to a thermal treatment at 90° C., possess the desired controlled release property. In fact, the time required to release 90% of the initial acetaminophen tablet content is about 22 hours. Tablets recovered after the dissolution test (40 hours) were swollen and intact and had excellent mechanical properties (resistant and elastic).

On the other hand, tablets prepared with the product of example 1b were not as good and the time required to release 90% of the initial acetaminophen content was about 6 hours. Tablets recovered after the dissolution test (after 40 hours) showed cracks in the longitudinal axis of the tablet and had poor mechanical properties. Gel particles due to the tablet erosion were found in the dissolution medium.

Tablets prepared with the product of example 1c were completely disintegrated only after a few minutes of immersion in the dissolution medium.

Thus, the results reported hereinabove clearly demonstrate that the controlled release properties of the cross-linked high amylose starch are related to the intensity of the heat treatment applied to the aqueous product just before spray drying.

NMR analysis of cross-linked high amylose starch in powder form or in the form of dry pressed pellet has revealed that its general morphological aspect is characterized by a broad singlet at C1 position (103 ppm) which can be interpreted as an imperfect V form. The spectra of wetted pressed pellets (placed 48 hours in water before the NMR spectra were taken) made with cross-linked high amylose starch prepared as described in example 1a was realized according to the test method described earlier. The spectra of the wetted press pellets revealed a doublet at C1 position which can be interpreted by the transformation of amorphous amylose to the B form of amylose. Almost 77% of transformation into B amylose form was obtained after tablets hydration. It was possible to determine the relative % of the different polymorphs present in the mixture based on the deconvolution of curves obtained by accumulating a high number of scans for each spectrum. The relative % of B form was calculated as the sum of the peaks area at 100–101 ppm and the relative % of the V form was considered as the area of the peak at 103 ppm.

In conclusion, NMR results seem to demonstrate that the tablet gelification is characterized by a shift from the V form to the B form of amylose during hydration.

EXAMPLE 2

This example was carried out in the same manner as example 1, with the exception that the product recovered from the diafiltration was concentrated before thermal treatment and spray drying.

More particularly, the slurry of cross-linked high amylose starch recovered from the diafiltration was concentrated by evaporation under vacuum in a APV evaporator type JPE having an evaporating capacity of 400 Kg of water/hr. In order to reduce its viscosity and to facilitate the operation, the product was heated up to 90° C. prior to being subjected to further concentration. Then, the concentration of cross-linked amylose slurry was carried out in the APV evaporator at a steam temperature in the range of 100° to 105° C. under a vacuum averaging of 23 inches of Hg. The outlet product temperature varied from 60° to 65° C. The concentration was carried out until a concentration of 6% w/w of solids was reached.

EXAMPLE 2a
Thermal treatment at 90° C.

The so obtained concentrated slurry of cross-linked high amylose starch (6% w/w) was heated up to 90° C. under stirring and kept at that temperature for 2 minutes. Then, the product was cooled to 70° C. under stirring and spray dried at 6% of solids in a Niro spray dryer having an inlet temperature of 300° C. and an outlet temperature of 130° C.

EXAMPLE 2b
Absence of thermal treatment

The obtained concentrated slurry of cross-linked high amylose starch (6% w/w) was cooled down to 50° C. under stirring. It was not subjected to any additional thermal treatment. Rather, it was directly spray dried in a Niro spray dryer having an inlet temperature of 300° C. and an outlet temperature of 125° C.

The "in Vitro" dissolution method described hereinabove was used to test the properties of the product prepared as presented in examples 2a and 2b. The obtained test results are reported in the following Table II.

TABLE II

|  | Time (h) required to release the following % of the initial drug content of the tablet | | |
|---|---|---|---|
|  | 30% | 60% | 90% |
| Example 2a | 3.0 | 9.0 | 21.0 |
| Example 2b | 3.0 | 9.0 | 22.0 |

The test results reported in the above Table II show that the products prepared as described in examples 2a and 2b both possess the desired controlled release property. In fact, tablets made of cross-linked high amylose starch prepared as described in examples 2a and 2b released 90% of the initial drug tablet content in 21 and 22 hours respectively. All the tablets recovered after the dissolution test (40 hours) were swollen, intact and had excellent mechanical properties (firm and elastic).

At first sight, these results would seem to demonstrate that it should be possible to avoid thermal treatment of the product before spray drying. However, this is not correct as a "kind" of thermal treatment was actually carried out further during the concentration of the product (the temperature of the evaporator plate varied in the range of 100° to 105° C.). Thus, it seems that such heating was sufficient to obtain the same effect as is obtained by a separate thermal treatment carried out for 2 minutes at 90° C.

From an industrial standpoint, it is believed that it is preferable to apply systematically a separate heat treatment to the product, just before spray drying, as is described in example 2a hereinafter, in order to ensure batch reproducibility.

EXAMPLE 3
Precipitation with ethanol

This example was carried out in the same manner as in example 1, with the exception that the product recovered from the diafiltration was concentrated as in example 2a to reach a concentration of 8.1% w/w of solids; then it was subjected to a thermal treatment and, finally, it was precipitated with ethanol prior to being spray dried in order to reduce the viscosity.

More specifically, the obtained concentrated product (8,1% w/w) was heated up to 90° C. under stirring and kept at that temperature for 2 minutes. Then, the product was cooled down to 30° C. and pure anhydrous ethanol was added to the slurry in order to obtained a final ethanol concentration of 30% w/w. The product was cooled down to 4° C. and spray dried at 5.5% of solids in a Niro® spray dryer having an inlet temperature of 280° C. and an outlet temperature of 98° C.

Controlled release property was evaluated according to the "in Vitro" dissolution tests described hereinabove. The test results are reported in Table III.

TABLE III

|  | Time (h) required to release the following % of the initial drug content of the tablet | | |
|---|---|---|---|
|  | 30% | 60% | 90% |
| Example 3 | 2.5 | 8.0 | 20.0 |

The above-described treatment of the cross linked high amylose starch with ethanol permitted to reduce significantly the viscosity and facilitated spray drying. The "in vitro" dissolution results show that it is possible to reduce the product viscosity by the addition of ethanol without modifying the controlled release property. Indeed, the time required to release 90% of the initial acetaminophen tablets content was about 20 hours.

Tablets recovered after the dissolution test (40 hours) were swollen, intact and possessed excellent mechanical properties (firm and elastic).

Based on the arguments presented hereinabove in the description of the prior art, it must be stressed out that even if the benefit effect of ethanol on product viscosity is useful, the real purpose of the present invention is to manufacture cross-linked high amylose starch possessing the desired properties without any organic solvent. Accordingly, this step should be preferably avoided.

EXAMPLE 4
Wet granulation process

The powder recovered from the spray drier in example 3 was wet granulated in a Glatt® fluid bed granulator model GPCG-15. The fluidization and humidification of the product powder was carried out in the fluid bed chamber at an inlet temperature of 30° C. and a dew point of 20° C. for a specific period of time needed to reach a moisture content of 5.5%. Then, 0.38 Kg of water per Kg of powder was introduced at a flow rate of 130 g/min into the fluid bed by a spray nozzle having an aperture of 1.2 mm and a spray angle of 45°. The granulation was carried out at an inlet temperature of 30° C., at a dew point of 15° C. and at an initial air volume of 10 m$^3$/h. The granulated product was dried in the fluid bed granulator at an inlet temperature of 60° C. and at an initial air volume of 750 m$^3$/h until a moisture content of 11% was reached.

The particle size distribution of the wet granulated product obtained in this example was determined according to the method described hereinafter. As discussed earlier, the purpose of granulation is to enlarge the particle size and obtain uniform particles which will flow through the tablet machine hopper and feed frame into the dies. The particle size distribution of the granulated product that was so obtained is reported in the following Table IV.

TABLE IV

| | Particle size distribution | | | | | |
|---|---|---|---|---|---|---|
| | <75 μm | 75–150 μm | 150–250 μm | 250–355 μm | 355–850 μm | >850 μm |
| Relative % | 17.0 | 22.7 | 21.3 | 12.5 | 19.3 | 7.2 |

Most of the granules obtained were larger than 75 μm and about 76% were in the range of 75 to 850 μm.

The controlled released property of the so obtained cross-linked high amylose starch was evaluated using the "in vitro" dissolution test described hereinabove. To do so, tablets having a diameter of 13 mm and a thickness of 2.9 mm were prepared by direct compression of a mixture powder of 300 mg of cross-linked high amylose starch, 100 mg of acetaminophen as a model drug, and 100 mg of HPMC K100M (hydroxypropyl methyl cellulose) in a hydraulic press at 2.4 T/cm$^2$.

The obtained results are reported in the Table V.

TABLE V

| | Time (h) required to release the following % of the initial drug content of the tablet | | |
|---|---|---|---|
| | 30% | 60% | 90% |
| Example 4 | 2.5 | 9.0 | 19.0 |

These dissolution test results show that the granulated product prepared as described in example 4 had the requested controlled release property and were releasing 90% of the initial drug content of the tablets in about 19 hours.

EXAMPLE 5

Preparation of cross-linked high amylose starch using a thermomechanical gelatinization pretreatment and epichlorohydrin as cross-linking agent Gelatinization:

A high amylose starch containing 70% w/w of amylose was first gelatinized. To do so, 266 Kg of an aqueous dispersion of the high amylose starch at a concentration of 14% w/w solids was introduced at a rate of 1 Kg/mn in an Alpha-Laval CONTHERM® scraped-surface heat exchanger for 50 minutes at 160° C. The recovered gelatinized product was kept under stirring at 65° C. until the next step.

Cross-linking reaction of the high amylose starch with epichlorohydrin

About 124 Kg of the product recovered from the gelatinization step were transferred to a 200 L GOAVEC scraped surface, stirred crystallization tank. The pH of the medium was raised up by the addition of about 3.1 Kg of sodium hydroxide at 27% w/w. Under maximum stirring, 0.535 Kg of epichlorohydrin was introduced into the gelatinized high amylose starch and the reaction was carried out at 50° C. for 3 hours. After reaction, the mixture was diluted with 71 Kg of water at 60° C. Then, the mixture was neutralized with an acetic acid solution (23% w/w) to obtain a pH below 8. The neutralized mixture was diluted with about 680 Kg of water at 50° C. and cooled to 4° C., and it was kept at that temperature until next step.

Removal of by-products, concentration and thermal treatment

Removal of by-products and thermal treatment were carried out in the same manner as described in the example 1a with the exception that the product was cooled to 30° C. under stirring and spray dried in a Niro spray dryer having an inlet temperature of 300° C. and an outlet temperature of 125° C.

As mentioned hereinabove, the reaction conditions may vary depending on the type and quantity of cross-linking agent used as well as the batch size, the starch content, the sodium hydroxide concentration, and the like. In this example, the reaction was carried out under lower sodium hydroxide concentration than in the previous examples. In order to obtain the same desired properties, the quantity of epichlorohydrin was then slightly increased and the reaction time was prolonged to 3 hours.

The controlled release property was evaluated according to the "in Vitro" dissolution test described hereinabove.

The tablets made with cross-linked high amylose starch prepared as described in this example, possessed good controlled release property. The time required to release 90% of the initial acetaminophen tablets content was about 18 hours and the tablets demonstrated good mechanical properties (relatively firm and elastic).

Thus, it appears that even if the use of a thermomechanical gelatinization step requires some adjustment of the reaction parameters, replacement of the chemical gelatinization with such thermomechanical gelatinization does not alter the desired controlled release properties of the final product.

EXAMPLE 6

Preparation of cross-linked high amylose starch using a thermomechanical gelatinization pretreatment and trimetaphosphate (STMP) as cross-linking agent Gelatinization The gelatinization of the high amylose starch used as starting material was carried out in the same manner as described in example 5.

Cross-linking reaction of the high amylose starch with STMP

Then, about 124 Kg of the product recovered from the gelatinization step were transferred in a 200 L GOAVEC crystallization tank and the pH was raised up with the addition of about 3.1 Kg of sodium hydroxide at a concentration of 27% w/w. Under maximum stirring, 0.84 Kg of trisodium trimetaphosphate was introduced into the gelatinized high amylose starch and the reaction was carried out at 50° C. for 3 hours. After reaction, the mixture was diluted with 71 Kg of water at 60° C. Then, the mixture was neutralized with an acetic acid solution (23% w/w) to obtain a pH below 8. The neutralized product was diluted with about 680 Kg of water at 50° C. and cooled to 4° C. It was kept at that temperature until the next step.

Removal of by-products and thermical treatment

Removal of the by-products and thermal treatment were realized in the same manner as presented in example 1a with the exception that the product containing 3.52% w/w of solids was cooled to 70° C. under stirring and spray dried in a Niro spray dryer having an inlet temperature of 300° C. and an outlet temperature of 125° C.

The controlled release property of the product prepared in this example was evaluated according to the "in vitro" dissolution test described hereinabove. The test results are reported in Table VI. The NMR spectra of the dry powder form of this product and the wetted press pellets according to the NMR method were also realized.

TABLE VI

| | Time (h) required to release the following % of the initial drug content of the tablet | | |
|---|---|---|---|
| | 30% | 60% | 90% |
| Example 6 | 1.0 | 4.5 | 13.0 |

It is known in the prior art that epichlorohydrin as cross-linking agent can successfully be replaced by trisodium trimetaphosphate (STMP). The reaction of STMP with starch leads to the preparation of a polymer bounded with phosphorous groups and increases the polymer affinity for water.

It is also known in the prior art that the swelling properties and the viscosity of the cross-linked starch with the STMP are unexpectedly superior to the one cross-linked with epichlorohydrin.

Therefore, based on the reported properties of the starch cross-linked with STMP, it was not obvious that high amylose starch cross-linked with STMP would have the requested controlled release property. In fact, the phosphorous groups would have been presumed to act like electrolytic agents and pump the water from the dissolution medium into the tablet and were supposed to lead to an accelerated tablet disintegration. However, the tests carried out by the Applicant have shown that the cross-linked high amylose starch prepared with STMP in the manner described in example 6 had the good controlled release properties. As discussed in example 5 and earlier, the substitution of epichlorohydrin for STMP appears to be conditional to the adjustment of the other reaction parameters.

In any event, even if the reaction parameters are not fully optimized, the time required to release 90% of the initial acetaminophen tablets content was about 13 hours and the tablets demonstrated relatively good mechanical properties.

The RMN results showed the same transformation from the V form of amylose to the B form during hydration, thereby suggesting that the mechanism of gelification observed for the STMP cross-linked high amylose starch is almost the same as the one observed for the epichlorohydrin cross-linked amylose starch.

Of course, numerous modifications could be made to the present invention as disclosed and exemplified hereinabove, without departing from the scope of the appended claims.

What is claimed is:

1. A process for the industrial manufacture in an aqueous medium of a slow-release excipient consisting mainly of cross-linked amylose having controlled release properties for use in the preparation of tablets or pellets, said process comprising:
   (a) subjecting a starch containing a high amount of amylose, hereinafter called "high amylose starch", to a gelatinization;
   (b) cross-linking the gelatinized high amylose starch with 1 to 5 g of a cross-linking agent per 100 g of dry-based gelatinized high amylose starch in an alkali medium thereby forming a reaction medium containing a reaction product consisting of a cross-linked high amylose starch slurry;
   (c) neutralizing the reaction medium obtained in step (b), thereby forming by-products mainly consisting of salts, removing the by-products from said reaction medium to recover the cross-linked high amylose starch slurry, said removing being carried out in the absence of organic solvent;
   (d) subjecting the cross-linked high amylose starch slurry to a thermal treatment at a temperature of at least 60° C.; and
   (e) drying the thermally treated product obtained in step (d) to obtain the requested slow release excipient consisting mainly of cross-linked amylose in the form of solid particles.

2. The process of claim 1, wherein, in step (a), the gelatinization is carried out by chemical treatment of an aqueous dispersion of the high amylose starch with sodium hydroxide.

3. The process of claim 1, wherein, in step (a), the gelatinization is carried out by thermomechanical treatment of an aqueous dispersion of the high amylose starch using a scraped surface heat exchanger.

4. The process of claim 1, wherein, in step (b), the cross-linking is carried out at a pH of 10 to 14 and at a temperature of 20° to 60° C. for 0.5 to 40 hours.

5. The process of claim 4, wherein the cross-linking agent is selected from the group consisting of trisodium trimetaphosphate, epichlorhydrin, adipic-acetic anhydride and phosphorus oxychloride.

6. The process of claim 1, wherein, in step (c), the by-products are removed by an aqueous continuous ultrafiltration.

7. The process of claim 1, wherein in step (c), the recovered cross-linked high amylose starch slurry is concentrated in the absence of an organic solvent at a concentration lower than or equal to 10% w/w of solids.

8. The process of claim 7, wherein the concentration is carried out by evaporation under vacuum.

9. The process of claim 7, wherein the thermal treatment of step (d) is an integral part of the concentration carried out in step (c).

10. The process of claim 1, wherein, in step (d), the thermal treatment is carried out by heating the slurry at about 90° C. for about 2 minutes.

11. The process of claim 1, wherein, in step (e), the drying is carried out by lyophilization, and step (e) is followed by a pulverization.

12. The process of claim 1, wherein, in step (e), the drying is carried out by spray-drying of the slurry, and step (e) is followed by a wet granulation.

13. A process for the industrial manufacture in an aqueous medium of a slow-release excipient consisting mainly of cross-linked amylose having controlled release properties for use in the preparation of tablets or pellets, said process comprising:
   (a) subjecting a starch containing a high amount of amylose, hereinafter called high amylose starch, to a gelatinization by thermomechanical treatment of an aqueous dispersion of said high amylose starch using a scraped surface heat exchanger;
   (b) cross-linking the gelatinizing high amylose starch with 1 to 5 g of a cross-linking agent per 100 g of dry-based gelatinized high amylose starch in an alkali medium thereby forming a reaction medium containing a reaction product consisting of a cross-liked high amylose starch slurry, said cross-linking agent being selected from the group consisting of trisodium trimetaphosphate, epichlorhydrin, adipic-acetic anhydride and phosphorus oxychloride;
   (c) neutralizing the reaction medium obtained in step (b), thereby forming by-products mainly consisting of salts, removing by aqueous continuous ultrafiltration the by-products from said reaction medium in order to recover the cross-linked high amylose starch slurry, and concentrating the so recovered slurry by evaporation under vacuum, said removing and concentrating being carried out in the absence of an organic solvent;

(d) subjecting the cross-linked high amylose starch slurry to a thermal treatment at a temperature of at least 60° C.; and (e) drying the thermally treated product obtained in step (d) to obtain the requested slow release excipient consisting mainly of cross-linked amylose in the form of solid particles.

14. The process or claim 13, wherein, in step (d), the thermal treatment is carried out by heating the slurry at about 90° C. for about 2 minutes.

15. The process of claim 14, wherein, in step (e), the drying is carried out by lyophilization, and step (e) is followed by a pulverization.

16. The process of claim 14, wherein, in step (e), the drying is carried out by spray-drying of the slurry, and step (e) is followed by a wet granulation.

* * * * *